(12) United States Patent
Lee et al.

(10) Patent No.: US 9,034,200 B2
(45) Date of Patent: May 19, 2015

(54) PLASMA ETCHING OF DIAMOND SURFACES

(75) Inventors: Chee-Leong Lee, Berkshire (GB); Erdan Gu, Berkshire (GB); Geoffrey Alan Scarsbrook, Berkshire (GB); Ian Friel, Berkshire (GB); Martin David Dawson, Berkshire (GB)

(73) Assignee: Element Six Limited Technologies Limited (GB)

( * ) Notice: Subject to any disclaimer, the term of this patent is extended or adjusted under 35 U.S.C. 154(b) by 1107 days.

(21) Appl. No.: 12/523,956

(22) PCT Filed: Jan. 22, 2008

(86) PCT No.: PCT/IB2008/050215
§ 371 (c)(1),
(2), (4) Date: Oct. 9, 2009

(87) PCT Pub. No.: WO2008/090511
PCT Pub. Date: Jul. 31, 2008

(65) Prior Publication Data
US 2010/0047519 A1  Feb. 25, 2010

(30) Foreign Application Priority Data

Jan. 22, 2007 (GB) .................................. 0701186.9
Mar. 22, 2007 (GB) .................................. 0705523.9
Mar. 22, 2007 (GB) .................................. 0705524.7
May 21, 2007 (GB) .................................. 0709716.5
Jul. 11, 2007 (GB) .................................. 0713464.6

(51) Int. Cl.
*B44C 1/22* (2006.01)
*C03C 25/68* (2006.01)
(Continued)

(52) U.S. Cl.
CPC ............ *H01L 29/1602* (2013.01); *C23C 16/27* (2013.01); *C23C 16/274* (2013.01);
(Continued)

(58) Field of Classification Search
CPC ..... H01J 37/305; H01J 37/3053; H01J 37/31; H01J 27/02
USPC ....................................... 216/67, 94; 438/712
See application file for complete search history.

(56) References Cited

U.S. PATENT DOCUMENTS 5,276,338 A  1/1994  Beyer et al.
5,309,000 A  5/1994  Saito et al.
(Continued)

FOREIGN PATENT DOCUMENTS

EP   0343963 A2   11/1989
EP   0458530 A2   11/1991
(Continued)

OTHER PUBLICATIONS
"Non-neutral Plasmas", Wikipedia web page.*
(Continued)

*Primary Examiner* — Binh X Tran
*Assistant Examiner* — Thomas Pham
(74) *Attorney, Agent, or Firm* — Bryan Cave LLP

(57) ABSTRACT

The present invention relates to a method of producing a diamond surface including the steps of providing an original diamond surface, subjecting the original diamond surface to plasma etching to remove at least 2 nm of material from the original surface and produce a plasma etched surface, the roughness $R_q$ of the plasma etched surface at the location of the etched surface where the greatest depth of material has been removed satisfying at least one of the following conditions: $R_q$ of the plasma etched surface is less than 1.5 times the roughness of $R_q$ of the original surface, or $R_q$ of the plasma etched surface is less than 1 nm.

19 Claims, 8 Drawing Sheets

(51) Int. Cl.

| | | |
|---|---|---|
| C03C 15/00 | (2006.01) | |
| C23F 1/00 | (2006.01) | |
| C23F 3/00 | (2006.01) | |
| H01L 29/16 | (2006.01) | |
| C23C 16/27 | (2006.01) | |
| C30B 25/10 | (2006.01) | |
| C30B 25/20 | (2006.01) | |
| C30B 29/04 | (2006.01) | |
| G01N 27/30 | (2006.01) | |
| H01L 21/02 | (2006.01) | |
| H01L 21/04 | (2006.01) | |
| H01L 29/04 | (2006.01) | |
| H01L 29/167 | (2006.01) | |
| H01L 29/36 | (2006.01) | |

(52) U.S. Cl.
CPC ............. *C23C16/278* (2013.01); *C30B 25/105* (2013.01); *C30B 25/20* (2013.01); *C30B 29/04* (2013.01); *G01N 27/308* (2013.01); *H01L 21/02376* (2013.01); *H01L 21/02527* (2013.01); *H01L 21/02579* (2013.01); *H01L 21/0262* (2013.01); *H01L 21/02634* (2013.01); *H01L 21/041* (2013.01); *H01L 29/045* (2013.01); *H01L 29/167* (2013.01); *H01L 29/36* (2013.01); *H01L 21/02104* (2013.01)

(56) References Cited

U.S. PATENT DOCUMENTS

| | | | |
|---|---|---|---|
| 5,491,348 A | 2/1996 | Koyamao et al. | |
| 5,506,422 A | 4/1996 | Dreifus et al. | |
| 5,609,926 A | 3/1997 | Prins | |
| 5,803,967 A | 9/1998 | Plano et al. | |
| 6,013,191 A | 1/2000 | Nasser-Faili et al. | |
| 6,177,292 B1 | 1/2001 | Hong et al. | |
| 6,207,282 B1 | 3/2001 | Deguchi et al. | |
| 6,252,725 B1 | 6/2001 | Tran et al. | |
| 6,605,352 B1 | 8/2003 | Windischmann | |
| 6,652,763 B1 | 11/2003 | Wei et al. | |
| 7,740,824 B2 | 6/2010 | Godfried et al. | |
| 2001/0015319 A1* | 8/2001 | Choe et al. | 204/408 |
| 2003/0076643 A1* | 4/2003 | Chu et al. | 361/93.9 |
| 2004/0256624 A1 | 12/2004 | Sung | |
| 2005/0035283 A1* | 2/2005 | Hieftje et al. | 250/285 |
| 2005/0109262 A1 | 5/2005 | Linares et al. | |
| 2005/0127373 A1 | 6/2005 | Yokota et al. | |
| 2005/0155543 A1 | 7/2005 | Meguro et al. | |
| 2005/0255691 A1* | 11/2005 | Ding et al. | 438/627 |
| 2006/0231015 A1 | 10/2006 | Meguro et al. | |
| 2007/0231473 A1* | 10/2007 | Suwa et al. | 427/130 |
| 2008/0117509 A1* | 5/2008 | Hayashi et al. | 359/486 |
| 2008/0121897 A1 | 5/2008 | LaRoche et al. | |

FOREIGN PATENT DOCUMENTS

| | | |
|---|---|---|
| EP | 0496564 A1 | 7/1992 |
| EP | 0697738 A1 | 2/1996 |
| EP | 0741118 A2 | 11/1996 |
| EP | 0994074 A2 | 4/2000 |
| EP | 1536043 A1 | 7/2005 |
| EP | 1555337 A2 | 7/2005 |
| EP | 1571241 A1 | 9/2005 |
| EP | 1712661 A1 | 10/2006 |
| EP | 2189555 A2 | 5/2010 |
| GB | 2281254 A | 3/1995 |
| GB | 2358409 A | 7/2001 |
| GB | 2252202 A | 7/2002 |
| GB | 2428690 A | 2/2007 |
| JP | 60246627 A | 12/1985 |
| JP | S63-220524 A | 9/1988 |
| JP | 03205339 A | 6/1991 |
| JP | 05139889 A | 8/1993 |
| JP | 05-299635 A | 11/1993 |
| JP | 2001-247965 A | 9/2001 |
| JP | 2002 057167 A | 2/2002 |
| JP | 2002-075960 A | 3/2002 |
| JP | 2002-118257 A | 4/2002 |
| JP | 2003-347580 A | 12/2003 |
| JP | 2004292172 A | 10/2004 |
| JP | 2004-538230 A | 12/2004 |
| JP | 2005-263592 A | 9/2005 |
| JP | 2006-080376 A | 3/2006 |
| JP | 2006-507204 A | 3/2006 |
| JP | 2006076851 A | 3/2006 |
| JP | 2006 216716 A | 8/2006 |
| WO | 99 22049 A1 | 5/1999 |
| WO | 2001013404 A1 | 2/2001 |
| WO | 01 75197 A1 | 10/2001 |
| WO | 01 96633 A1 | 12/2001 |
| WO | 01 96634 A1 | 12/2001 |
| WO | 03 014427 A1 | 2/2003 |
| WO | 03 052174 A2 | 6/2003 |
| WO | 2004 027123 A1 | 4/2004 |
| WO | 2005 074013 A2 | 8/2005 |
| WO | 2006 013430 A1 | 2/2006 |
| WO | 2006-044164 A2 | 4/2006 |
| WO | 2006 061707 A2 | 6/2006 |
| WO | 2006-076354 A2 | 7/2006 |
| WO | 2006 117621 A1 | 11/2006 |
| WO | WO 2006117621 A1 * | 11/2006 |
| WO | 2007 066215 A2 | 6/2007 |

OTHER PUBLICATIONS

A.R. Lang, "The Properties of Diamond," Chapter 14 "Internal Structure," Ed. J.E. Field, Academic Press London 1979, p. 434.

Hirakuri et al., "The Effect of Ultrasonic Vibration on CVD Diamond Nucleation," Diamond & Related Materials 6, 1997, 1031-1035.

Ariki et al., "Efficient field effect in heavily doped thin-film diamond metal-insulator-semiconductor diode employing BaTiO3 insulator film", Japanese Journal of Applied Physics, vol. 33, pp. L888-L891 (1994).

Choi et al., "Properties of natural diamond microlenses fabricated by plasma etching," Industrial Diamond Review, Issue 2, 2005, pp. 29-31.

Choi et al., "Fabrication and Evaluation of GaN Negative Bifocal Microlenses," Journal of Applied Physics, 97 (2005), 063101-1-063101-3.

Choi et al., Fabrication of natural diamond microlenses by plasma etching, J. Vac. Sci. Technol. B, 23 (2005), 130-132.

Crisman et al., "Large pyroelectric response from reactively sputtered aluminum nitride thin films," Electrochemical and Solid-State Letters, 8, 2005, pp. H31-H32.

Denisenko et al., "Diamond power devices. Concepts and Limits," Diamond and Related Materials, vol. 14, No. 3-7, pp. 491-498.

Enlund et al., "Anisotropic dry etching of boron doped single crystal CVD diamond," Carbon, 43, pp. 1839-1842.

"Ion Backscattering Analysis," in Concise Encyclopedia of Material Characterization, R.W. Cahn and E Lifshin, eds., Pergamon (London), 1993, pp. 199-204.

Karlsson et al., "Transfer of continuous-relief diffractive structure into diamond by use of inductively coupled plasma dry etching," Optics Letters, 26, 2001, pp. 1752-1754 (p. 215-217).

Karlsson et al., "Transfer of micro-optical structures into GaAs and diamond," Proceedings of the SPIE, vol. 4561, 2001, pp. 114-122.

Koide, Y., "Analysis for Electron Concentrations in n-diamond/III-nitride heterostructure and phosphorus delta-doped structure in diamond", Japanese Journal of Applied Physics, vol. 44, 2005, pp. 55-59.

Koide, Y., "Enhancement of donor ioinization in phosphorus-doped n-diamond", Applied Surface Science, col. 244, pp. 26-29 (2205).

Kondo et al., "Homoepitaxial single-crystal boron-doped diamond electrodes for electroanalysis," Journal of the Electrochemical Society, vol. 149, No. 6, Jun. 2002, pp. E179-E184.

Kondo et al., "Plasma etching treatment for surface modification of boron-dopied diamond electrodes," Electrochimica Acta, 52, 2007, 3841-3842.

(56) References Cited

OTHER PUBLICATIONS

Lee, et al., "Fabrication and characterization of diamond micro-optics," Diamond and Related Materials 15, 2006, pp. 725-728.
Miskys C. et al., "AlN/diamond heterojunction diodes", Applied Physics Letters, vol. 82, pp. 290-292 (2003).
Miskys C. R. et al., "Structural and interface properties of an AlN diamond ultraviolet light emitting diode", Applied Physics Letters, vol. 83, pp. 3699-3701 (2004).
Nebel C. et al., "AlN/diamond np-junctions," Diamond and Related Materials, 12, 2003, pp. 1873-1876.
Okumura, H., "Present status and future prospect of widegap semiconductor high-power devices," Japanese Journal of Applied Physics, 45, 2006, 7565-7586.
Pearton "ECR plasma etching of chemically vapour deposited diamond thin films," Electronics Letters, Apr. 1992, pp. 822-824.
Samlenski et al., "Characterisation and lattice location of nitrogen and boron in homoepitaxial CVD diamond," Diamond and Related Materials, vol. 5, No. 9, Jul. 1996, pp. 947-951.
Sine et al., "Electrochemical behavior of fluorinated boron-doped diamond," Electrochemical and Solid-State Letters, 6, 2003, D9-11.
Tavares et al., "{111}-oriented diamond films and p/n. junctions grown on B-doped type Ib substrates," Diamond and Related Materials, vol. 14, No. 3-7, Mar. 2005, pp. 522-525.
Vogg et al., "High quality heteroepitaxial AlN films on diamond," Journal of Applied Physics, 96, 2004, 895-902.
International Search Report for PCT/IB200/050214 dated May 27, 2008.
International Search Report for PCT/IB200/050215 dated May 28, 2008.
International Search Report for PCT/IB200/050216 dated May 27, 2008.
International Search Report for PCT/IB200/050218 dated Jun. 13, 2008.
International Search Report for PCT/IB200/050219 dated Jun. 16, 2009.
UK Search Report for GB0709716.5 dated Sep. 21, 2007.
UK Search Report for GB0701186.9 dated Jul. 5, 2007.
UK Search Report for GB0705524.7 dated Jul. 16, 2007.
UK Search Report for GB0713464.6 dated Oct. 26, 2007.
UK Search Report for GB0705523.9 dated Jul. 20, 2007.
Ramesham et al., "Air-Microwave Plasma Etching of Polycrystalline Diamond Thin Films," J. Electrochem. Soc., 139, 1988, 1992.
Karlsson et al., "Diamond micro-optics: microlenses and antireflection structured surfaces for the infrared spectral region," Optics Express, vol. 11, No. 5, 2003, pp. 502-507.
Partial European Search Report for EP 13 17 4114 dated Feb. 13, 2014.

* cited by examiner

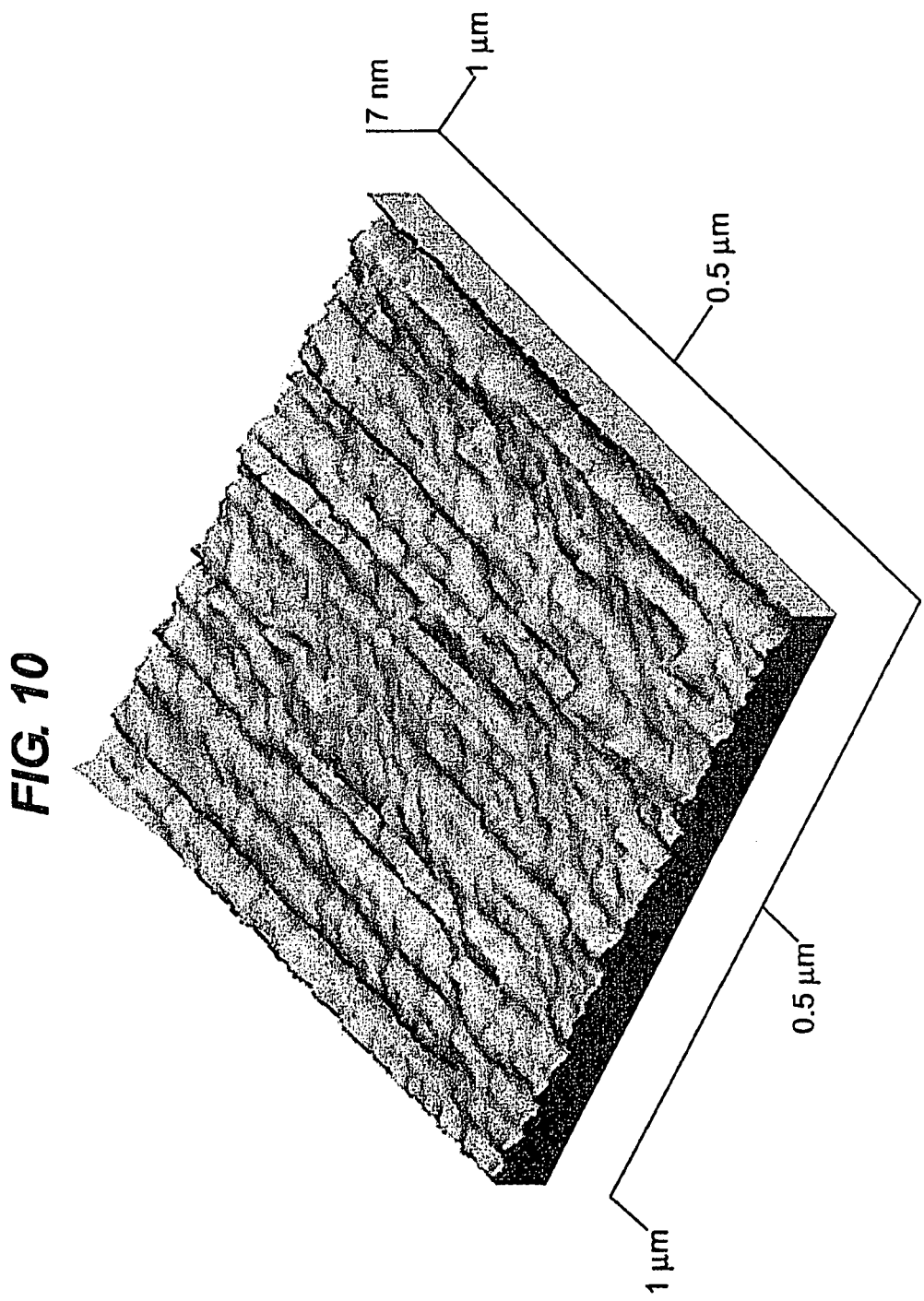

PLASMA ETCHING OF DIAMOND SURFACES

BACKGROUND TO THE INVENTION

Diamond is a difficult material to form into complex structures because of its hardness and chemical inertness. Traditionally diamond has been shaped by lapidary techniques such as lapping and polishing using fine diamond grits and powders as the abrasive medium. One typical product of such processes is faceted natural diamonds used as jewellery. Examples of industrial products formed by lapidary processes are polycrystalline diamond plates used as exit windows for high power $CO_2$ lasers. In all these cases, the finished diamond product has large flat surfaces (i.e. extending laterally greater than a few 10 s of micrometers), ostensibly free from surface features which affect the performance.

The use of lapidary processes on diamond has the disadvantage that they result in the surface being processed having a 'damaged zone' that extends to a depth roughly equal to the diamond particle size used for processing.

For applications that require fine three-dimensional surface structural features, lapidary methods are not suitable. Liquid chemical etching processes, such as are used extensively in the microelectronics industry are not applicable to diamond because diamond is resistant to almost all chemicals.

High temperature gas phase etching processes have been used to etch diamond. The use of hydrogen-argon-oxygen and hydrogen-argon plasmas at high temperature (>700° C.) to etch substrates prior chemical vapour deposition (CVD) diamond synthesis is disclosed in WO 01/96633. Such an etch preferentially etches damage features associated with the sub-surface damage layer and therefore the roughness $R_q$ is generally significantly increased as a result of the etch process.

In typical reactive ion etching (RIE) processes, large numbers of ions are produced that are accelerated towards the target and physically remove material by sputtering and related processes. The process can have low selectivity between materials and therefore is not always ideal for patterning surfaces. EP1555337 discloses the use of a reactive ion etch (RIE) using an oxygen-carbon fluoride ($O_2$—$CF_4$) gas mixture at a pressure of 1.33-13.3 Pa (about 10-100 mTorr) to prepare mechanically processed single crystal diamond surfaces for CVD growth.

In contrast to RIE, inductively-coupled plasma (ICP) etching is a largely chemical process in which a plasma is used to breakdown the etching gases into a mixture of free radicals (i.e. neutral species) and ions (i.e. charged species). The plasma is remote from the substrate being etched. Between the plasma and the diamond being etched, the vast majority of the ions generated in the plasma are removed. Thus the majority of species that reach the diamond are neutral. The resulting etching is therefore largely chemical (e.g. surface reactions leading to volatile products), rather than physical (e.g. sputtering from the surface by ions from the plasma). Since atoms in a higher energy state in the substrate, such as those in a region with extended lattice imperfections (e.g. a damaged region), are easier to etch, then this type of etch generally preferentially etches the regions of extended lattice imperfections, roughening the surface.

The use of inductively-coupled plasma (ICP) etching with an argon-oxygen gas mixture to pattern natural single crystal diamond is reported in H. W. Choi et al, 'Properties of natural diamond microlenses fabricated by plasma etching', Industrial Diamond Review, Issue 2, 2005, page 29, and to pattern polycrystalline diamond made by a chemical vapour deposition process in M. Karlsson et al, 'Transfer of continuous-relief diffractive structure into diamond by use of inductively coupled plasma dry etching', Optics Letters, 26 (2001), 1752-1754. UK Patent Application GB 2 281 254 discloses the use of a mixture of oxygen and fluorine containing gases in a plasma etching method for diamond. No disclosure is made about the roughness of the etched surfaces.

ICP etching of gallium nitride (GaN) using an $Ar/Cl_2$ gas mixture is reported in H. W. Choi et al, Journal of Applied Physics, 97 (2005), 063101.

SUMMARY OF THE INVENTION

The invention is a method of producing a diamond surface by plasma etching from an original surface which may be prepared by a traditional lapidary process, lapping or polishing or just polishing or from an as-grown surface. The invention also extends to a diamond surface, or portion of a diamond surface, which has been produced using the method of the invention.

According to a first aspect to the present invention there is provided a method of producing a diamond surface including the steps of providing an original diamond surface, subjecting the original diamond surface to plasma etching to remove at least 2 nm of material from the original surface and produce a plasma etched surface, the roughness Rq of the plasma etched surface at the location of the etched surface where the greatest depth of material has been removed satisfying at least one of the following conditions:

a. Rq of the plasma etched surface is less than 1.5 times the roughness of Rq of the original surface, or
b. Rq of the plasma etched surface is less than 1 nm.

Preferably both conditions are satisfied.

In a second aspect, the present invention provides a method of producing a diamond surface including the steps of providing an original diamond surface which has been mechanically processed; and subjecting the original diamond surface to plasma etching to remove at least 2 nm of material from the original surface and produce a plasma etched surface, wherein the plasma etched surface is substantially free from residual damage due to mechanical processing.

In the first and second aspects of the invention, preferably the diamond is CVD diamond, most preferably single crystal CVD diamond.

Preferably at least one structural feature is etched into either part of or all of the surface.

Preferably the plasma etching utilises an isotropic etch, preferably an Inductively-coupled plasma. The gas mixture used in the plasma etching may contain an inert gas and a halogen containing gas. Preferably the inert gas is argon.

The halogen containing gas may contain chlorine in which case preferably the halogen containing gas is molecular chlorine ($Cl_2$).

Preferably, in a method according to the present invention:
the maximum depth of the etched structural feature in a direction perpendicular to the original surface of the diamond is preferably less than 20 μm, and,
the smallest lateral dimension of the structural feature is preferably at least 0.5 times the maximum depth of the feature.

According to a third aspect of the present invention there is provided a method of producing an etched diamond surface including the steps of providing a diamond surface and subjecting the diamond surface to inductively coupled plasma etching using a gas mixture containing an inert gas and a halogen containing gas.

Preferably the diamond is CVD diamond, most preferably single crystal CVD diamond.

Alternatively the diamond may be polycrystalline CVD diamond.

According to a fourth aspect to the present invention there is provided a single crystal diamond having an etched surface or part of an etched surface resulting from at least 2 nm having been removed from a surface or a part of a surface of the diamond by etching, the etched surface having an Rq of less than 1 nm.

Preferably the diamond is CVD diamond.

The etching method is preferably a method according to the first, second and third aspects to the present invention as hereinbefore described.

According to a fifth aspect to the present invention there is provided a polycrystalline CVD diamond comprising an etched surface or part of an etched surface resulting from at least 0.5 μm having been removed from a surface or a part of a surface of the diamond by etching, the etched surface having a surface roughness Rq of less than 5 nm.

The etching method is preferably a method according to the first, second and third aspects to the present invention as hereinbefore described.

The polycrystalline CVD diamond may be for use in an optical device.

The plasma etching process removes at least about 2 nm, preferably at least about 5 nm, preferably at least about 10 nm, preferably at least about 20 nm, preferably at least about 50 nm, preferably at least about 100 nm, preferably at least about 200 nm, preferably at least about 500 nm, preferably at least about 1000 nm, from the original surface or part of the original surface.

The plasma etching process preferably removes between about 2 nm and about 50 μm, more preferably between about 2 nm and about 20 μm, still more preferably between about 2 nm and about 10 μm, and still more preferably between about 2 nm and about 5 μm from the original surface.

The plasma etched surface of the invention has a roughness $R_q^A$ (After the etch) and the original surface a roughness $R_q^B$ (Before the etch), such that $R_q^A/R_q^B$ is preferably less than about 1.5, more preferably less than about 1.4, more preferably less than about 1.2, more preferably less than about 1.1. Typically $R_q^B$ is prepared to an $R_q$ of less than about 10 nm, more typically less than about 3 nm, more typically less than about 1 nm, more typically less than about 0.5 nm prior to the etch.

The $R_q^B$ and $R_q^A$ measurements are taken on the same area of the diamond. By "same area" Is meant an equivalent area as close as reasonably practical, using multiple measurements and statistical analysis where necessary to verify the general validity of the measurements, as is known in the art.

The particularly unusual advantage of this plasma etch is that it can improve the $R_q$ of the diamond surface, particularly when applied to surfaces where the initial surface $R_q^B$ is prepared to an $R_q$ of less than about 1 nm, more typically less than about 0.5 nm, more typically less than about 0.3 nm, thus providing a route to extremely low surface roughness values. Under these circumstances, the plasma etched surface of the invention has a roughness $R_q^A$, and the original surface before the etch a roughness, $R_q^B$, such that $R_q^A/R_q^B$ is less preferably less than about 1.0, more preferably less than about 0.8, more preferably less than about 0.6, more preferably less than about 0.5, more preferably less than about 0.4, more preferably less than about 0.3.

The method thus provides a plasma etched diamond surface with an $R_q$ value preferably less than about 1 nm, preferably less than about 0.5 nm, preferably less than about 0.3 nm, preferably less than about 0.2 nm, preferably less than about 0.1 nm. Furthermore this plasma etched diamond surface with low $R_q$ preferably is largely free of processing damage such that the number of defects revealed by the revealing etch test is less than about 100 per $mm^2$.

For the purposes of this invention the roughness of a surface is described by its $R_q$ value. $R_q$ is also known as the 'root mean square' (or RMS) roughness. $R_q$ is defined as the square root of the mean squared deviations from the centre-line or plane of the surface profile:

$$R_q = \sqrt{((y_1^2 + y_2^2 + \ldots + y_n^2)/n)}$$

where $y_1^2$ etc are the squared deviations from the centre-line or plane of the surface profile and n is the number of measurements.

A surface may also be quantified by its $R_a$ value (also referred as 'average roughness' or 'centre line average'):

$$R_a = (|y_1| + |y_2| + \ldots |y_n|)/n$$

where $|y_1|$ etc are the moduli of the deviations from the centre-line or plane of the surface profile and n is the number of measurements.

For a surface with a Gaussian distribution of deviations from the centre-line or plane of the surface profile, the value of $R_q = 1.25 \times R_a$.

$R_a$ and $R_q$ may be measured along lines (a one-dimensional measurement) or over areas (a two-dimensional measurement). An area measurement is essentially a series of parallel line measurements.

For the purposes of this invention the $R_q$ value is normally measured over an about 1 μm by about 1 μm area or about 2 μm by about 2 μm area using a scanning probe instrument such as an atomic force microscope (AFM). In certain circumstances, it is considered more appropriate to measure the $R_q$ using a stylus profilometer over a 0.08 mm scan length.

The phrase 'structural feature' or 'topographic feature' is used throughout this specification to refer to desirable features or structure etched into the diamond in a controlled fashion, to provide useful function. In particular this is distinct from features arising in the surface of the diamond from anisotropic etching of sub-surface damage, which are referred to as 'damage features'

There are a number of application areas for this invention, each using a particular combination of the benefits given by this invention:

i) The preparation of structural features suitable for use in electronic structures such as transistor gate trenches etc. Such structural features in electronic structures are preferably in the range of about 2 nm to about 100 nm in depth, more preferably in the range about 2 nm to about 30 nm in depth. The method of this invention can provide low and controlled etch rates, with etch rates preferably less than about 0.08 μm/min, more preferably less than about 0.06 μm/min, more preferably less than about 0.04 μm/min, which etch rate varies in a relatively linear fashion with ICP coil power. Furthermore, the incubation time, or delay time at the start of the etch between applying the external process conditions and obtaining etching is small, typically less than about 5 seconds, more typically less than about 3 seconds, and consistent, so that precise etch depth control can be achieved. The isotropic nature of the etch of this invention gives surfaces where the presence of any damage features after the etch do not significantly roughen the surface, or more preferably where the etched surface is even smoother than the initially prepared surface, as described above.

ii) The preparation of structural features in the surface of the diamond for use in optical applications such as microlenses, and other applications needing relatively large topographic features, particularly with smooth curved surfaces. Such topographic features are preferably in the range of about 200 nm to about 20 μm in depth or vertical height of the features formed, more preferably in the range about 500 nm to about 5 μm in depth or vertical height of the features formed. The method of this invention can provide controlled etch rates, with etch rates preferably greater than about 0.08 μm/min, more preferably greater than about 0.10 μm/min, which etch rate varies in a relatively linear fashion with ICP coil power. Furthermore, the incubation time, or delay time at the start of the etch between applying the external process conditions and obtaining etching is small, typically less than about 5 seconds, more typically less than about 3 seconds, and consistent, so that precise etch depth control can be achieved. A particular benefit of this method is the low etch selectivity, made use of by applying a variable thickness of mask and enabling the etch to break through the mask to the diamond in at least some regions. The low etch selectivity enables relatively thick layers of mask to be used, reducing tolerances and difficulty in applying this layer, for the same final structural features in the diamond. The etch selectivity in applications of this type is preferably less than about 0.16, more preferably less than about 0.14, more preferably less than about 0.12, more preferably less than about 0.10, more preferably less than about 0.09. The etch selectivity is defined as:

(etch rate of mask)/(etch rate of diamond)

The isotropic nature of the etch of this invention gives surfaces where the presence of any damage features after the etch do not significantly roughen the surface, or more preferably where the etched surface is even smoother than the initially prepared surface, as described above.

iii) The preparation of surfaces or surface regions for further epitaxial growth, preferably for further growth of CVD diamond, or for preparing surfaces free of damage for electrical contacts on, for example, Schottky diodes, three-terminal electronic devices (such as field effect transistors) radiation detectors, sensors etc. Such preparation requires the removal of sufficient depth to significantly reduce the surface damage and thus needs to be of the same order of thickness as the surface damage layer. Typically surface damage layers have thicknesses in the range of about 0.2 μm to about 20 μm (or thicker with very aggressive lapidary techniques). Thus preferably the etch removes a thickness of material from the surface, where the thickness of material removed is at least about 0.2 μm, more preferably at least about 0.5 μm, more preferably at least about 1.0 μm, more preferably at least about 2 μm, more preferably at least about 5 μm, more preferably at least about 10 μm. The surface damage layer typically has a thickness that is about the same as the size of the largest diamond grit particle used for the last stage of lapidary processing; for example a surface scaife polished with 1-2 μm sized diamond grit will typically have a surface damage layer about 2 μm thick. Therefore, to minimise the amount of damage from lapidary processing that remains after etching by the method of the invention, the amount of material removed by the method of the invention should preferably be at least about 0.2 times the size of the largest grit particles, more preferably at least about 0.5 times the size of the largest grit particles, more preferably at least about 0.8 times the size of the largest grit particles, more preferably at least about 1.0 times the size of the largest grit particles, more preferably at least about 1.5 times the size of the largest grit particles, more preferably at least about 2 times the size of the largest grit particles. There is benefit in the surface roughness after such an etch remaining low, to avoid defects in the overgrown layer arising from damage features etched into the diamond surface. In particular, where the surface is single crystal diamond the surface preferably has a surface roughness after the etch, $R_q$, of less than about 10 nm, more preferably less than about 5 nm, more preferably less than about 2 nm, more preferably less than about 1 nm, more preferably less than about 0.5 nm, more preferably less than about 0.3 nm. Alternatively, where the surface is polycrystalline CVD diamond the surface preferably has a surface roughness after the etch, $R_q$, of less than about 40 nm, more preferably less than about 20 nm, more preferably less than about 10 nm, more preferably less than about 5 nm, more preferably less than about 2 nm, more preferably less than about 1 nm. The method of this invention can provide controlled etch rates, with etch rates preferably greater than about 0.08 μm/min, more preferably greater than about 0.10 μm/min, which etch rate varies in a relatively linear fashion with ICP coil power. Furthermore, the incubation time, or delay time at the start of the etch between applying the external process conditions and obtaining etching is small, typically less than about 5 s, more typically less than about 3 s, and consistent, so that precise etch depth control can be achieved. The isotropic nature of the etch of this invention gives surfaces where the presence of any damage features after the etch do not significantly roughen the surface, or more preferably where the etched surface is even smoother than the initially prepared surface, as described above.

The maximum depth of an etched structural feature in a direction perpendicular to the major surface of the diamond is preferably less than about 20 microns, more preferably less than about 10 microns, more preferably less than about 5 microns, more preferably less than about 2 microns, more preferably less than about 1 micron, more preferably less than about 500 nm, more preferably less than about 200 nm, more preferably less than about 100 nm, more preferably less than about 60 nm, and the smallest lateral dimension of the etched structural feature is preferably at least about 0.5 times the maximum depth, more preferably at least about 1 times the maximum depth, more preferably at least about 2 times the maximum depth, more preferably at least about 5 times the maximum depth, more preferably at least about 10 times the maximum depth, more preferably at least about 15 times the maximum depth.

In an embodiment, the present invention provides a method of producing a diamond surface including the steps of providing an original diamond surface, subjecting the original diamond surface to plasma etching, preferably isotropic plasma etching, more preferably inductively-coupled plasma etching to remove at least 2 nm of material from the original surface and produce a plasma etched surface, the roughness $R_q$ of the plasma etched surface at the location of the etched surface where the greatest depth of material has been removed satisfying at least one of the following conditions:
  a. $R_q$ of the plasma etched surface is less than 1.5 times the roughness of $R_q$ of the original surface, or
  b. $R_q$ of the plasma etched surface is less than 1 nm; and wherein, preferably the gas mixture used in the plasma etching contains an inert gas, preferably argon and a halogen containing gas, preferably chlorine.

The invention provides, according to another aspect, a single crystal diamond having an etched surface or part of an etched surface resulting from at least about 2 nm having been removed from a surface or a part of a surface of the diamond by etching, the etched surface having an $R_q$ of less than about 1 nm.

The invention provides according to yet another aspect, a polycrystalline CVD diamond comprising an etched surface or part of an etched surface resulting from at least about 0.5 µm having been removed from a surface or a part of a surface of the diamond by etching, the etched surface having a surface roughness $R_q$ of less than about 5 nm.

In an embodiment, the invention provides a single crystal diamond having an etched surface or part of an etched surface resulting from at least about 2 nm having been removed from a surface or a part of a surface of the diamond by etching, the etched surface having an $R_q$ of less than about 1 nm, preferably less than about 0.5 nm, preferably less than about 0.3 nm, preferably less than about 0.2 nm, preferably less than about 0.1 nm.

In another embodiment, the invention provides a polycrystalline CVD diamond comprising an etched surface or part of an etched surface resulting from at least about 0.5 µm having been removed from a surface or a part of a surface of the diamond by etching, the etched surface having a surface roughness $R_q$ of less than about 5 nm, preferably less than about 2 nm, preferably less than about 1 nm, preferably less than about 0.5 nm, preferably less than about 0.3 nm, preferably less than about 0.2 nm, preferably less than about 0.1 nm.

The plasma etched surface can either be in the form of the whole extent of a diamond surface or a proportion of the surface such as structural features etched into the surface as part of the process for making electronic devices, optical elements such as micro-lenses, micro-electro-mechanical systems (MEMS), X-ray optical elements etc.

The method of the invention results in a surface or surface structural features that, after undergoing the plasma etching process, are essentially free of the damage characteristic of diamond surfaces prepared by the traditional processes such as lapidary processes of either lapping and polishing or just polishing.

The extent of sub-surface damage can be revealed and quantified using a deliberately anisotropic thermal revealing etch. The revealing etch preferentially oxidises regions of damaged diamond and therefore allows such regions to be identified and thereafter quantified. Regions containing sub-surface damage from mechanical processing are typically darkened or even blackened by the revealing etch.

The revealing etch consists of:
(i) examining the surface at a magnification of 50 times using reflected light with a typical metallurgical microscope to ensure that there are no surface features present,
(ii) exposing the surface to an air-butane flame thereby raising the diamond surface to a temperature of typically about 800° C. to about 1000° C. for a period of about 10 seconds,
(iii) examining the surface at a magnification of 50 times using reflected light with a typical metallurgical microscope and counting the damage features revealed by the revealing etch, in the manner described below, to determine their number density,
(iv) repeating steps (ii) and (iii) and comparing the measured density of defects with that of the previous cycle until the following condition is met: if the number density of defects counted is less than or equal to about 150%, preferably less than or equal to about 120%, of the number density determined in the previous cycle, then all the defects are deemed to be revealed and the measurement recorded is the average of the measurements of the last two cycles, if not the cycle is repeated again.

The number density of defects is measured by the following method:
(i) the defects to be counted are those defects visible at a magnification of 50 times with a typical metallurgical microscope which fall totally or partially within a rectangular area 1 mm×0.2 mm projected onto the surface being characterised,
(ii) the area is selected at random over the surface or portion of the surface to be characterised and randomly oriented,
(iii) the defects are counted in a minimum of 5 such areas,
(iv) the number density of defects is calculated by dividing the total number of defects counted by the total area examined to give a number density in defect per mm$^2$.

To measure the number density of defects in areas less than about 1 mm$^2$ the above method is adapted by completing the defect count over the whole area as a single measurement.

For the surface to be considered to be substantially free of residual damage due to mechanical processing the number density of defects revealed in a surface of single crystal CVD diamond prepared by the method of the invention is less about 100 mm$^2$, preferably less than about 50 per mm$^2$, preferably less than about 20 per mm$^2$, preferably less than about 10 per mm$^2$, preferably less than about 5 per mm$^2$.

Alternatively, the technique of "Rutherford backscattering" (or "RBS") may be used to at least semi-quantitatively evaluate the extent of sub-surface damage in a sample. The technique of RBS is well known in the art (for example see the article "Ion Backscattering Analysis" in "Concise Encyclopedia of Materials Characterization", Eds R. W. Cahn and E. Lifshin, Pergamon (London), 1993, pages 199-204). RBS is an ion beam technique that that can probe up to about 1 µm beneath the surface of a crystalline solid. Information about the crystallographic perfection of the near surface layer can be obtained by the use of "channelling", wherein the higher the crystallographic perfection of the surface layer, the lower the backscatter ion yield, such that for a perfect surface, there is substantially no backscattered ion yield (where substantially means less than about 5%, preferably less than about 3%, preferably less than about 2%, preferably less than about 1%, of the incident ions are backscattered).

The surface of the invention is produced by plasma etching, preferably using an inductively-coupled plasma (ICP) etching process, and preferably at an operating pressure in the range of about 0.5 mTorr (about 0.0667 Pa) to about 100 mTorr (about 13.3 Pa), more preferably in the range of about 1 mTorr (about 0.133 Pa) to about 30 mTorr (about 4.00 Pa), more preferably in the range about 2 mTorr (about 0.267 Pa) to about 10 mTorr (1.33 Pa). The etchant is preferably a gas mixture consisting of at least an inert gas, preferably argon, and a halogen-containing gas, preferably chlorine ($Cl_2$). Preferably the halogen containing gas is present in the gas mixture added to the process in a concentration (by volume) in the range about 1%-about 99%, more preferably about 20%-about 85%, more preferably about 40%-about 70%. Preferably the majority of the balance of the gas mixture is made up with Ar, more preferably the whole of the balance of the gas is made up with Ar.

Alternatively the inert gas may be helium, neon, krypton or xenon, or may comprise a mixture of more than one of these, or may comprise a mixture of one or more of these with argon.

The plasma etching process of the invention is essentially a chemical process, therefore it etches diamond surfaces of all orientations at approximately the same rate, that is, the process can be described as being 'isotropic'. Therefore the process can be used to etch polycrystalline CVD diamond, a polished surface of which typically contains grains in a variety of orientations relative to the surface.

The method of the invention is compatible with conventional lithographic processes that might be used for the fabrication of electronic devices. For example it might be used to produce structural features on the surface of a diamond by applying a suitable resist to the surface, appropriately patterning the resist and then etching the surface using the same ICP process as previously described.

The method of the invention can be applied to surfaces comprising natural single crystal diamond, synthetic single crystal diamond made by high pressure-high temperature (HPHT) techniques, synthetic single crystal diamond made by CVD techniques ('single crystal CVD diamond'), and synthetic polycrystalline diamond made by CVD techniques ('polycrystalline CVD diamond').

The method of the present invention gives the following advantages over the prior art:
- the method can be used to pattern a surface with structural features, the patterning being done using standard lithographical methods,
- the method can be used to etch both single crystal and polycrystalline diamond without revealing pits due to dislocations in the former and grain boundaries in the latter,
- the method can be used to etch damaged surfaces without preferentially removing the damaged regions and hence without significantly roughening the surfaces,
- the method can be used to remove damage and hence prepare damage-free surfaces for epitaxial growth,
- the method can be used to remove damage and hence prepare damage-free surfaces for electrical contact formation,
- the method can be used on the surfaces of optical components,
- the roughness of the surface is not significantly increased by undertaking the etching process,
- the diamond surfaces obtained after removing sufficient material by etching can be essentially free of damage associated with mechanical surface processing.

The plasma etched diamond surface of the present invention can be used for a wide range of applications, including, for example, preparation of substrates for electronic device manufacture free of a damage layer, preparation of substrates for synthesis of homoepitaxial diamond layers by chemical vapour deposition, fabrication of three-dimensional structural features and surface preparation to enable high performance electrical contacts to be made to the surface.

It is surprising that diamond can be etched using an Ar-Hal, particularly an Ar—$Cl_2$, gas mixture. Diamond is a highly unreactive solid. Halogens are known to stabilise the surface of diamond during CVD growth processes which occur at temperatures between 500° C. and 1200° C. Inert gases are often used as charged species in PVD etching process, but in ICP the component of etching attributed to charged species is negligible.

As used herein, the term "about x" is intended to include the value x itself.

Thus, the invention provides according to yet another aspect a method of producing an etched diamond surface including the steps of providing a diamond surface and subjecting the diamond surface to inductively coupled plasma etching using a gas mixture containing an inert gas, preferably argon and a halogen containing gas, preferably chlorine.

BRIEF DESCRIPTION OF THE FIGURES

The following figures are referred to in examples 1 to 6.

FIG. 10 is an atomic force microscopy image of the HPHT diamond sample in FIG. 9 following Ar/Cl ICP plasma etching.

DETAILED DESCRIPTION OF THE EMBODIMENTS

Figure 1:
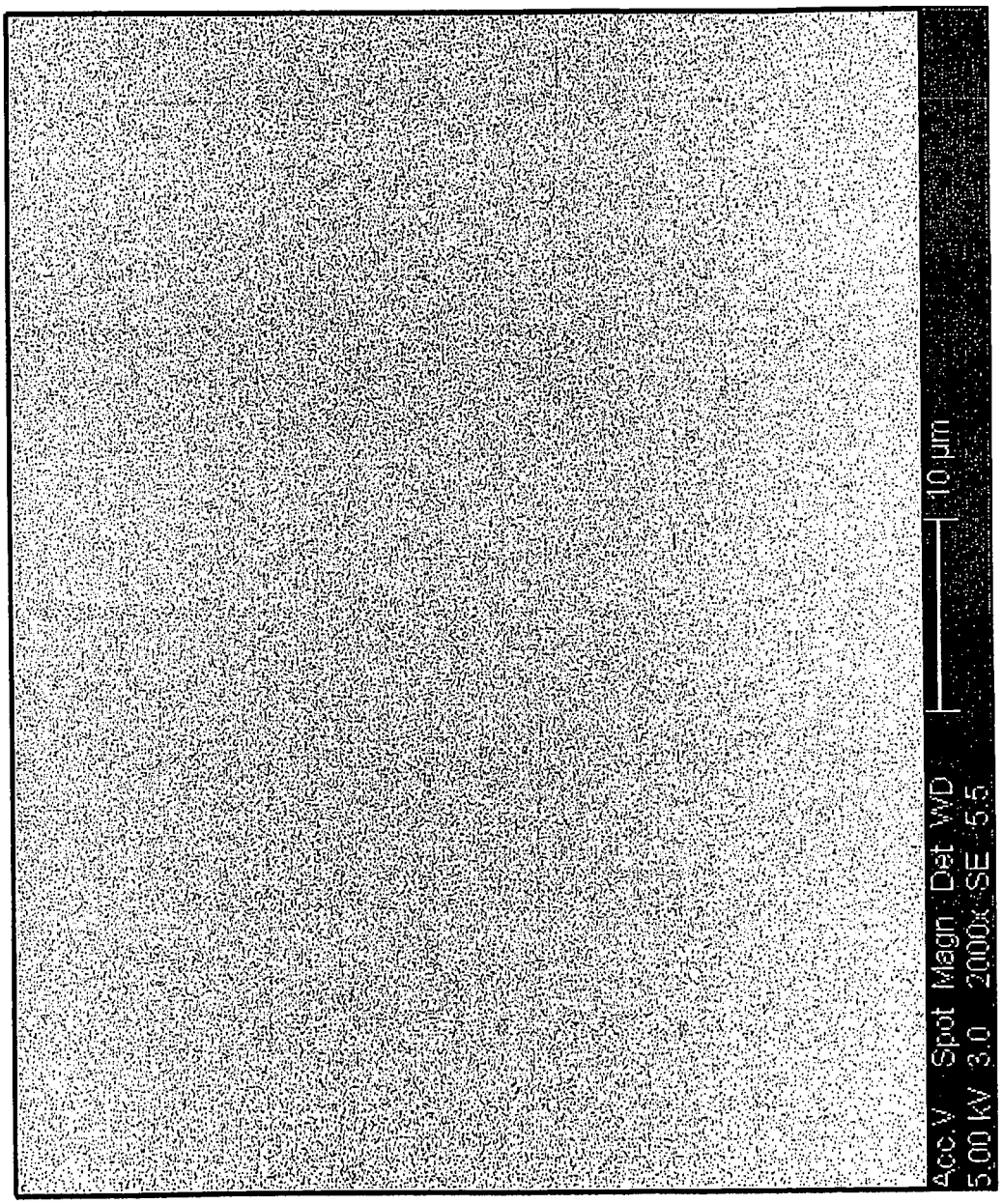
FIG. 1 is a scanning electron micrograph of an Ar/Cl ICP plasma etched trench approximately 16 nm deep.

The details of the invention will be described using six examples. The first example describes the use of the invention for making an essentially damage free surface on a series of single crystal CVD diamond plates and comparing the resultant surfaces with a sample that has not been etched. The second example describes the use of the invention for making fine structural features on a polycrystalline CVD diamond plate.

Example 1

Four single crystal CVD diamond plates approximately 4 mm×4 mm×0.5 mm were laser sawn from larger as-grown blocks of single crystal CVD diamond made by the method disclosed in WO 01/96633. The large planar surfaces of the plates (hereinafter referred to as the 'major surfaces') were oriented within a few degrees of {100} crystallographic surfaces. The smaller surfaces forming the edges of the plates (hereinafter referred to as the 'edge surfaces') were approximately parallel to <100> directions.

The major surfaces of all four plates were initially lapped on a cast iron lapping wheel using progressively finer diamond grit suspended in a cellulose-based carrier. The final lapping stage used diamond grit in the size range 15 µm to 25 µm and the roughness $R_q$ measured using a stylus profilometer over a 0.8 mm length was in the range 100 to 150 nm for all three plates. Previous experiments have indicated that after this stage of lapping, the sub-surface damaged layer extends to a depth of approximately 10 µm beneath the surface.

All of the plates were chosen at random and their major surfaces were polished using a traditional diamond polishing scaife. Two cast iron scaife-wheels were used, the first prepared with diamond powder in the size range 2-4 µm and the second with diamond powder in the size range 1-2 µm. The depth of material removed during the scaife polishing process was determined to be approximately 15 µm. After completion of the scaife processing, the $R_q$ values measured using a stylus profilometer over an 80 µm length were less than 5 nm. More accurate measurements over areas (e.g. about 1 µm by about 1 µm) made with an atomic force microscope gave the $R_q$ values listed in Table 1.

One of the plates (referred to as 'Sample 1') was selected at random and subjected to the thermal revealing etch according to the method previously described (heating the surface in air to about 850° C. for 10 seconds using a small air-butane blow torch). The defects were counted according to the method of the invention. The plate showed considerable evidence of sub-surface damage, very much greater than 100 defects per $mm^2$.

The other three plates (referred to as 'Sample 2', 'Sample 3' and 'Sample 4') were subjected to inductively coupled plasma etches to remove material from the surface. The ICP etching conditions were: a platen power of approximately 300 W, a coil power of approximately 400 W, a chamber pressure of 5 mTorr (0.667 Pa), flow rates of 25 sccm for Ar and 40 sccm for $Cl_2$. The etching times chosen for the three samples were 15, 30 and 60 minutes. The amount of material removed from the etched surfaces, the initial and final surface roughness, $R_q$, values are in Table 1.

TABLE 1

Characteristics of plates before and after plasma etching

| Sample | $R_q$ after scaife polishing, nm | Plasma etching time, minutes | $R_q$ after plasma etching, nm | Approximate depth of material removed, nm |
|---|---|---|---|---|
| 1 | 0.9 | N/A | N/A | N/A |
| 2 | 1.2 | 15 | 1.1 | 900 |
| 3 | 0.9 | 30 | 0.7 | 2000 |
| 4 | 0.7 | 60 | 0.5 | 4000 |

After the plasma etching process and after the measurement of the $R_q$, all three plates were subjected to the thermal revealing etch to evaluate the extent of sub-surface damage. For each of samples 2 to 4 the number density of defects measured was in each case less than 10, unlike that revealed in sample 1, which was the plate not subjected to the plasma etch.

Example 2

Two samples of polycrystalline CVD diamond about 10 mm×10 mm in lateral extent and about 650 µm thick were polished on their growth surfaces using conventional lapidary processes. The surface roughness values, $R_q$, of the polished plates, measured by atomic force microscopy over a 2 µm by 2 µm area were 1.0 nm and 1.0 nm.

Figure 2:
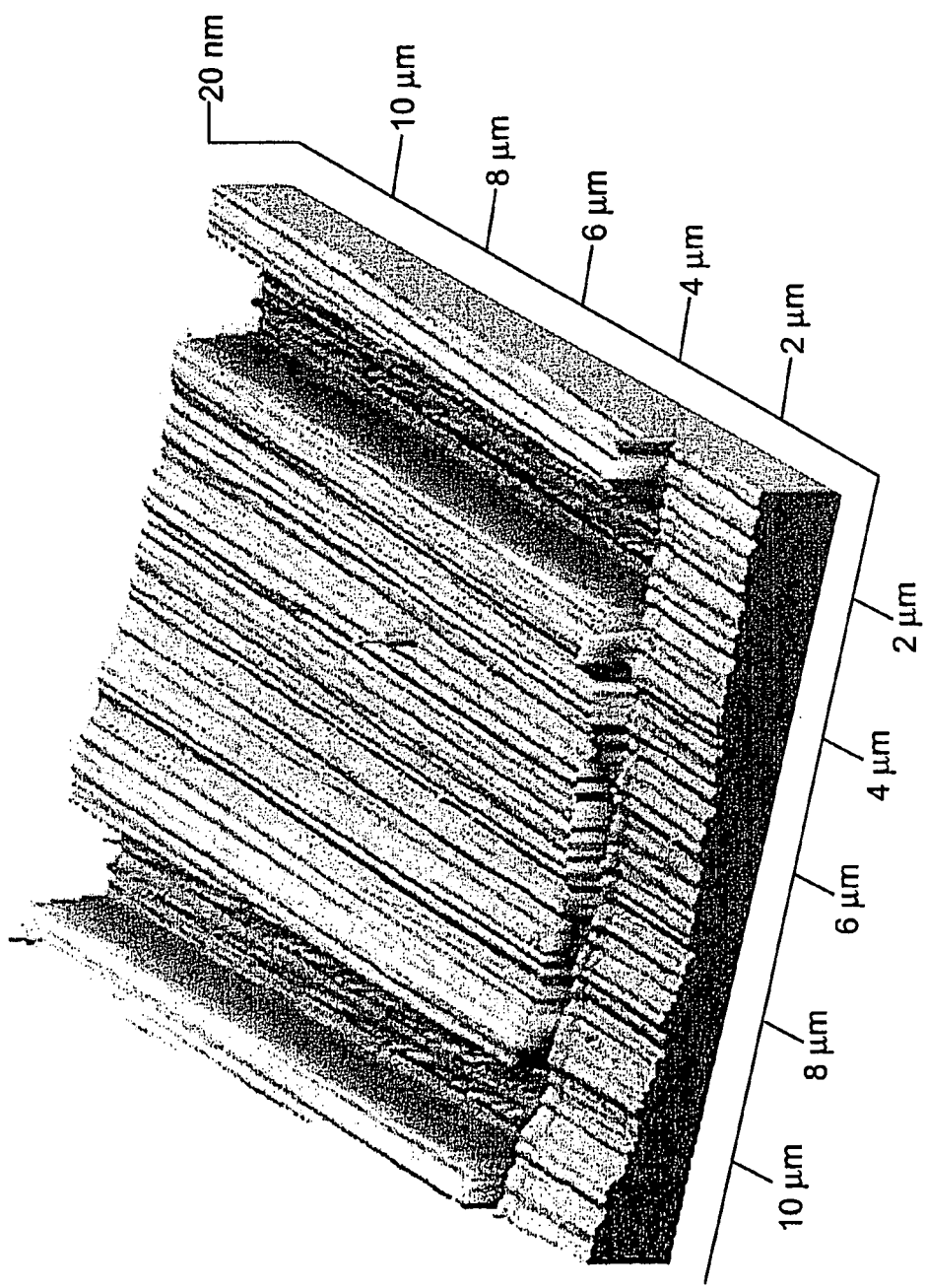
FIG. 2 is an atomic force microscopy image of a region of the trench in FIG. 1.
Figure 3:
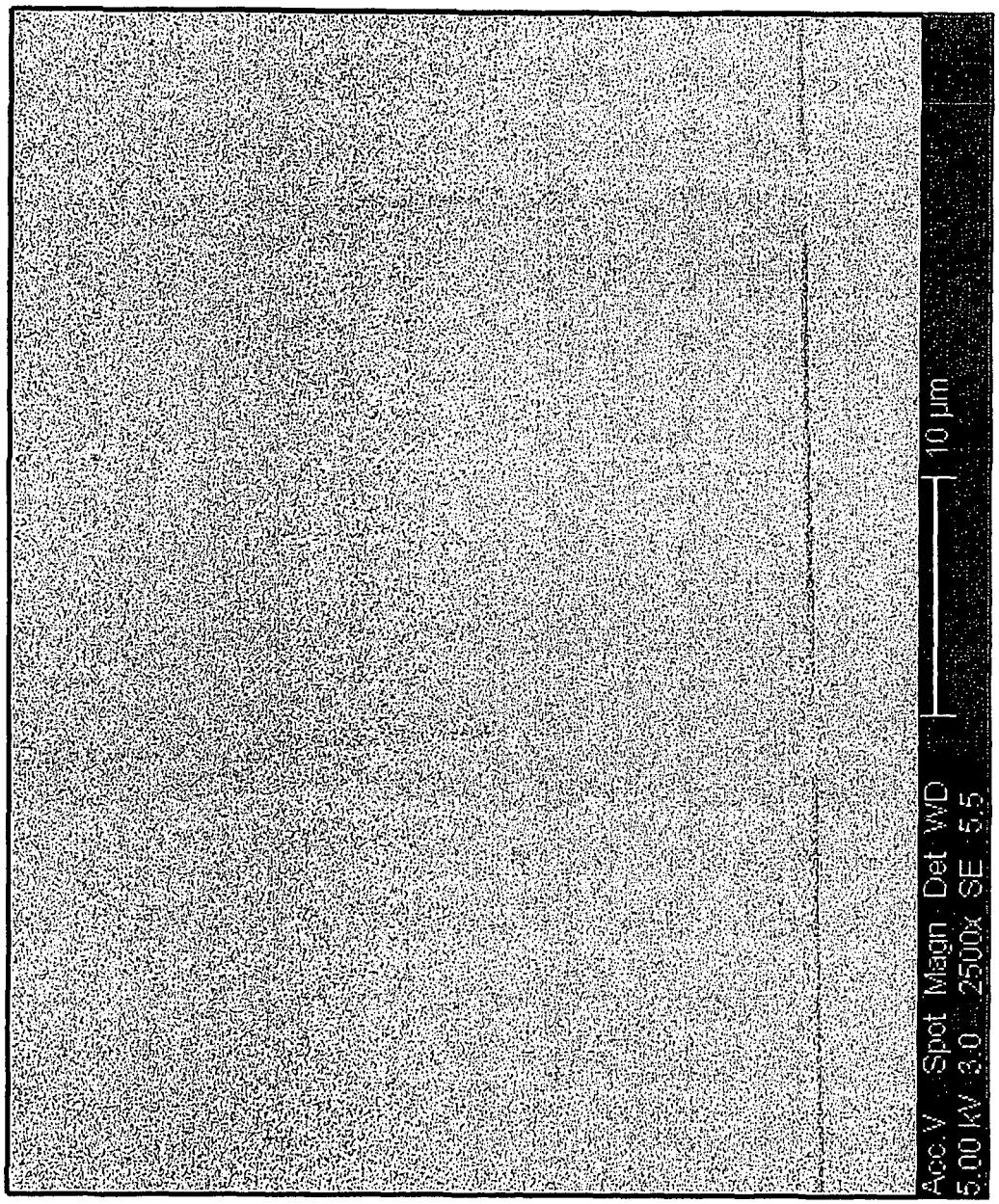
FIG. 3 is a scanning electron micrograph of an Ar/Cl ICP plasma etched trench approximately 53 nm deep.
Figure 4:
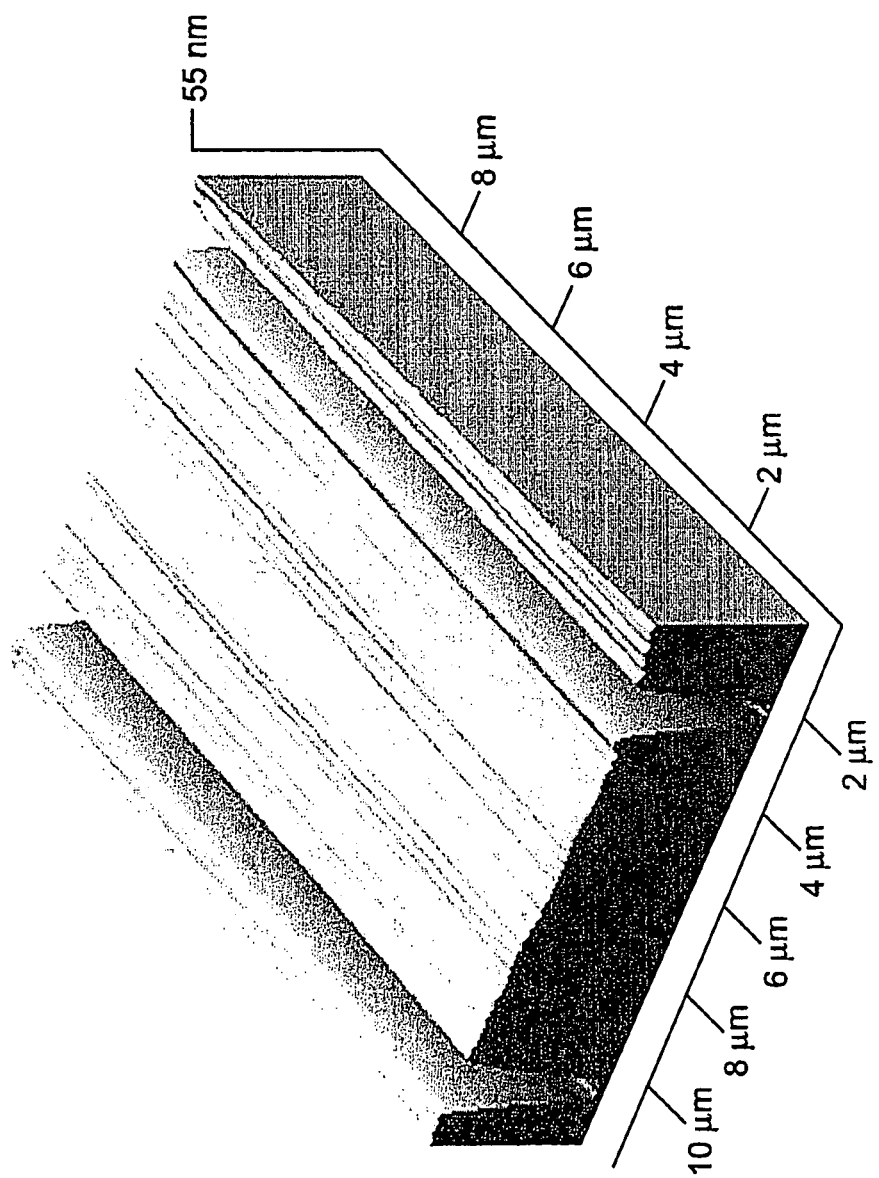
FIG. 4 is an atomic force microscopy image of a region of the trench in FIG. 3.

Micro-trenches were etched into the two samples of polycrystalline diamond using an Ar—$Cl_2$ ICP plasma. Micro-trench photoresist features were mask patterned on the surface of the samples using standard lithographic methods. The samples were etched using the following ICP chamber conditions: a platen power of approximately 300 W, a coil power of approximately 400 W, a chamber pressure of 5 mTorr (0.667 Pa), flow rates of 25 sccm for Ar and 40 sccm for $Cl_2$. In the first sample trenches of depth 16 nm were etched [FIG. 1 and FIG. 2] and in the second sample trenches of depth 53 nm were etched [FIG. 3 and FIG. 4]. It can be seen that the trench walls are well-defined, with no rough edges apparent. The etch rates were measured to be approximately 1 nm per second in both cases, which demonstrates the reproducibility of this method. It is also clear that the surfaces post-etch show no indication of the grain boundaries in these polycrystalline samples, which demonstrates that the etch is isotropic in nature. The $R_q$ values (measured over 1 µm×1 µm areas using an atomic force microscope) of the samples after etching the 16 and 53 nm deep trenches are 0.8 and 1.1 nm respectively, which should be compared to the pre-etched surface roughness of 1.0 nm. This indicates that under these conditions little or no surface roughening is caused using this etching method, and further supports the conclusion that the etch is isotropic.

Example 3

Spherical micro-lens structures were fabricated in a sample of single crystal IIa natural diamond using Ar/$Cl_2$ ICP etching in conjunction with the photoresist reflow method [H. W. Choi, E. Gu, C. Liu, J. M. Girkin, M. D. Dawson, J. of Appl. Phys. 97 (6), 063101 (2005); C. L. Lee, H. W. Choi, E. Gu, M. D. Dawson, Dia. Rel. Mat. 15, 725 (2006)]. A 7 µm thick layer of Shipley SPR220 photoresist was spin-coated onto the diamond substrate first. After mask patterning, the photoresist pillars were formed. The sample was then placed on a hotplate at 125° C. for 2 minutes to allow the photoresist pillars to re-flow. Due to the surface tension, spherical lens structures were formed. These lens structures were then transferred onto the diamond substrate by ICP etching using Ar/$Cl_2$ plasma. The ICP parameters used were: a platen power of 100 W, a coil power of 400 W, a chamber pressure of 5 mTorr (0.667 Pa), flow rates of 25 sccm for Ar and 40 sccm for $Cl_2$, with an etching duration of 25 minutes.

Figure 5:
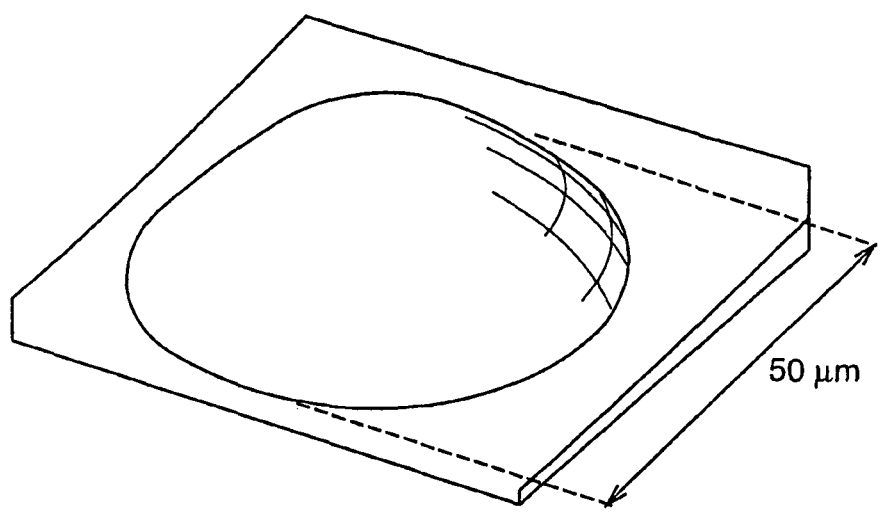
FIG. 5 is line drawing based on an atomic force microscopy image of an Ar/Cl ICP plasma etched diamond micro-lens
Figure 6:
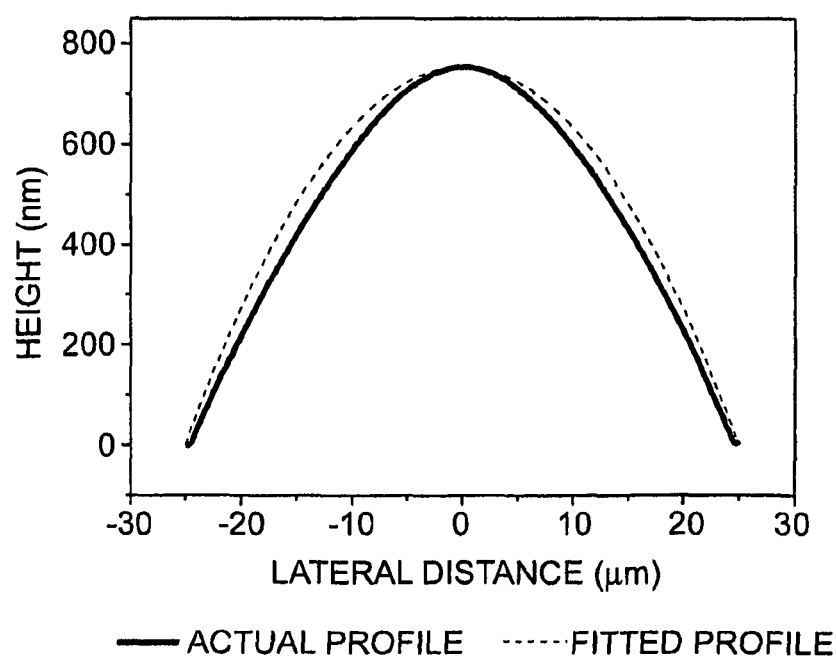
FIG. 6 is a measured line profile across the centre of the diamond micro-lens shown in FIG. 5, along with a fitted profile with ideal spherical curvature.

A line drawing based on an atomic force microscopy image of a representative diamond micro-lens is shown in FIG. 5. The surface diameter and height of the lens were measured to be 50 µm and 0.75 µm respectively. The profile of the diamond micro-lenses was studied by examining the cross-sectional scan of the atomic force microscopy images. The measured profile was then compared to the curvature of a circle. The measured cross-sectional profile of the diamond micro-lens and the fitted spherical profile are plotted in FIG. 6. It can be seen that the deviation from the ideal profile is very small, indicating the cross-sectional profile of the micro-lens is very close to spherical in shape.

Example 4

Figure 7:
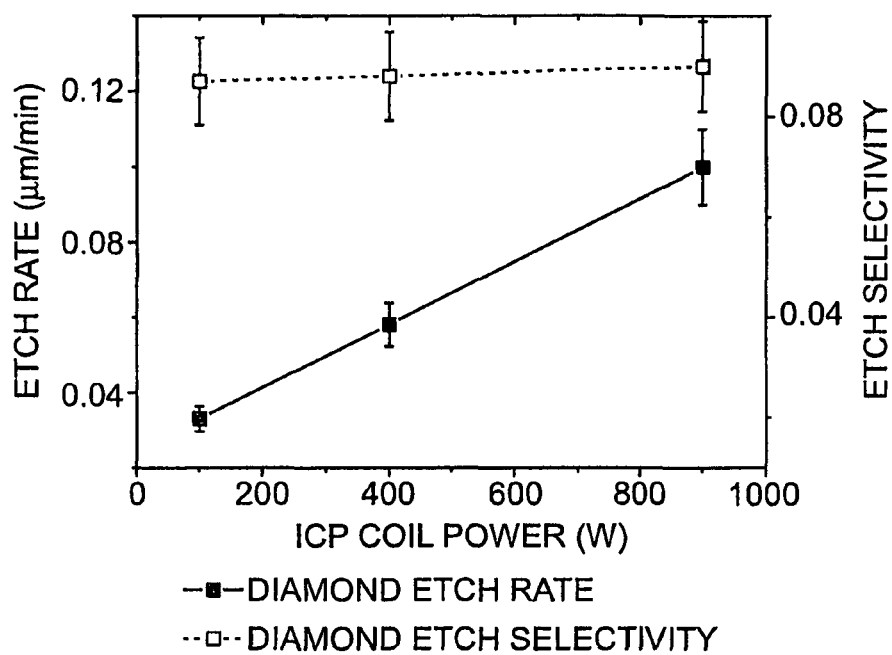
FIG. 7 is a plot of etch rate and etch selectivity against ICP coil power.

The etch rate and etch selectivity (as defined earlier) of the Ar/$Cl_2$ ICP plasma was investigated as a function of the ICP coil power using the following conditions: ICP coil powers of 100 W. 400 W and 900 W; a constant ICP platen power of 300 W; a chamber pressure of 5 mTorr (0.667 Pa); flow rates of 25 sccm for Ar and 40 sccm for $Cl_2$; an etching duration of 5 minutes. Single crystal natural diamond samples were used for these experiments and photoresist was used as the mask material. The results are plotted in FIG. 7. It is observed that the etch rate increases linearly with the ICP coil power and etch selectivity is approximately constant (at around 0.09). In a similar experiment the etch selectivity on type Ib synthetic single crystal diamond was also found to be around 0.09. This should be compared to the etch selectivity using an Ar/$O_2$ ICP plasma, which is around 0.20 [C. L. Lee, H. W. Choi, E. Gu, M. D. Dawson, Dia. Rel. Mat. 15, 725 (2006)]. Hence, using photoresist masks of identical thickness, the height or depth of microstructures fabricated in diamond (such as micro-lenses and micro-trenches) using ICP Ar/$Cl_2$ etching would be approximately half of those fabricated using ICP Ar/$O_2$ etching. Thus the lower etch selectivity obtained using Ar/$Cl_2$ is more suitable for etching shallower structural features into diamond in which precise control on the depth or height of the microstructure is required.

Example 5

Figure 8:
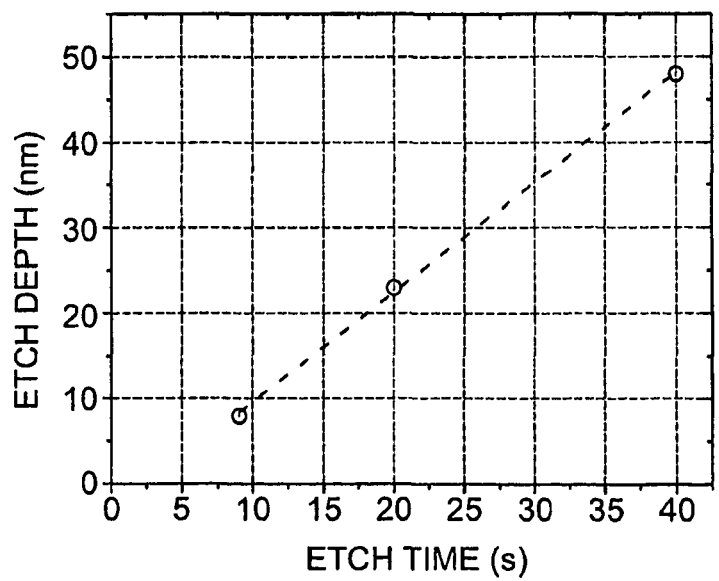
FIG. 8 is a plot of etch rate versus etch time.

Etch rate as a function of time was investigated by etching micro-trenches in type Ib synthetic single crystal diamond samples. Trenches were etched in three samples using identical photoresist masks and under Ar/$Cl_2$ ICP plasma conditions identical to those described in Example 2. The three samples were etched respectively for 9, 20 and 40 seconds. The depths of the micro-trenches formed were measured by atomic force microscopy and are plotted in FIG. 8 as a function of the etch time. The mean etch rate was extracted by performing a simple linear curve fit to the data, and found to be 1.29±0.03 nm $s^{-1}$. The small uncertainty in this number indicates that the method yields a reproducible etch rate, which is an important requirement of a manufacturing process.

Example 6

Figure 9:
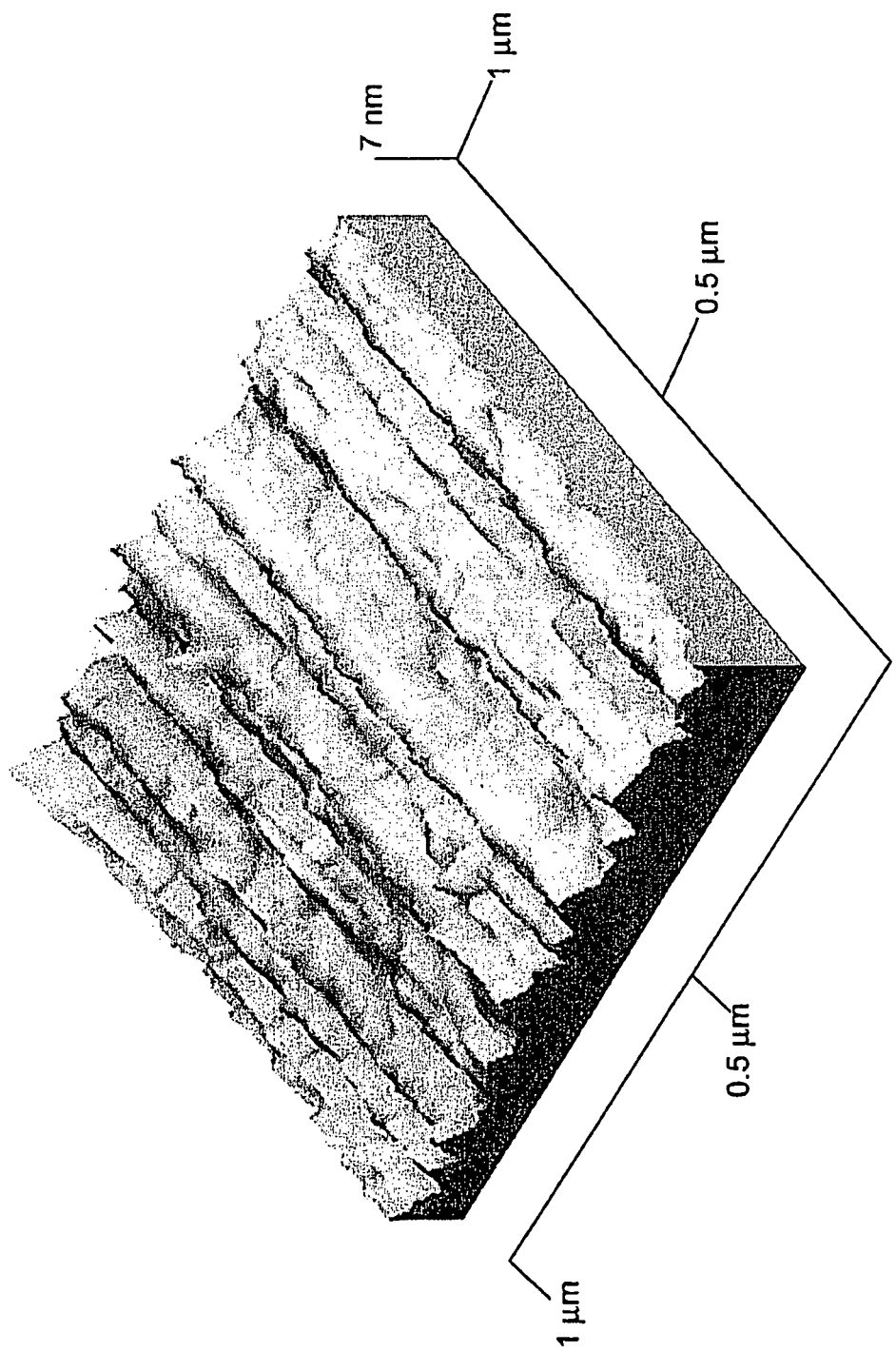
FIG. 9 is an atomic force microscopy image of a HPHT diamond surface polished using a resin-bonded wheel.

A type Ib HPHT single crystal sample, mechanically polished using a resin-bonded polishing wheel, was etched for 10 minutes using the following ICP chamber conditions: a platen power of approximately 300 W, a coil power of approximately 100 W, a chamber pressure of 5 mTorr (0.667 Pa), flow rates of 25 sccm for Ar and 40 sccm for $Cl_2$. FIG. 9 shows a representative atomic force microscope scan over a 1 μm×1 μm surface area of the polished sample prior to ICP etching. The surface is characterised by nanometer-scale linear trenches or grooves resulting from the polishing and the roughness $R_q$ over this area was measured to be 0.53 nm. FIG. 10 shows a representative AFM scan over a 1 μm×1 μm surface area of the sample after the ICP etch. It can be seen that the linear polishing grooves are shallower than before and the roughness $R_q$ over this area was measured to be 0.19 nm. This example demonstrates the ability of this method to reduce the roughness of mechanically pre-polished diamond surfaces.

The invention claimed is:

1. A method of producing an etched diamond surface including the steps of
    mechanically processing a diamond surface to have a roughness $R_q$ of less than 10 nm, wherein the mechanically processed diamond surface comprises a damaged zone extending to a depth of at least 2 nm as a result of the mechanical processing; and
    subjecting the mechanically processed diamond surface to plasma etching to remove at least 2 nm of material from the mechanically processed diamond surface thereby removing the damaged zone from the mechanically processed diamond surface and producing a plasma etched surface which has a number of defects, as revealed by a revealing plasma etch, of less than 100 per $mm^2$,
    wherein the plasma etching involves exposing the mechanically processed diamond surface to an inductively-coupled plasma etch;
    wherein the roughness $R_q$ of the plasma etched surface at the location of the etched surface where the greatest depth of material has been removed satisfies at least one of the following conditions:
        a. $R_q$ of the plasma etched surface is less than 1.5 times the roughness of $R_q$ of the mechanically processed diamond surface, or
        b. $R_q$ of the plasma etched surface is less than 1 nm;
    wherein the step of plasma etching the original surface utilizes a gas mixture consisting of inert gas and molecular chlorine ($Cl_2$), and the inert gas is selected from argon, helium, neon, krypton, xenon, and mixtures thereof; and
    wherein the inductively-coupled plasma etch removes material from the mechanically processed diamond surface by chemical surface reactions rather than physical sputtering as in a reactive ion etching process in which ions are accelerated towards a target surface to physically remove material therefrom.

2. A method according to claim 1 wherein both conditions a. and b. are satisfied.

3. A method according to claim 1, wherein at least one structural feature is etched into either a part of or all of the mechanically processed diamond surface.

4. A method according to claim 1, wherein at least one structural feature is etched into either a part of or all of the mechanically processed diamond surface, and wherein:
    a maximum depth of the etched structural feature in a direction perpendicular to the original surface of the diamond is less than 20 μm, and,
    the smallest lateral dimension of the structural feature is at least 0.5 times the maximum depth of the feature.

5. A method according to claim 1, wherein the roughness $R_q$ of the mechanically processed diamond surface is less than 3 nm.

6. A method according to claim 1, wherein the roughness $R_q$ of the mechanically processed diamond surface is less than 1 nm.

7. A method according to claim 1, wherein the roughness $R_q$ of the mechanically processed diamond surface is less than 0.5 nm.

8. A method according to claim 1, wherein the plasma etching removes at least 5 nm of material from the mechanically processed diamond surface.

9. A method according to claim 1, wherein the plasma etching removes at least 10 nm of material from the mechanically processed diamond surface.

10. A method according to claim 1, wherein the plasma etching removes at least 20 nm of material from the mechanically processed diamond surface.

11. A method according to claim 1, wherein the plasma etching removes at least 50 nm of material from the mechanically processed diamond surface.

12. A method according to claim 1, wherein the plasma etching removes at least 100 nm of material from the mechanically processed diamond surface.

13. A method according to claim 1, wherein the plasma etching removes at least 200 nm of material from the mechanically processed diamond surface.

14. A method according to claim 1, wherein the plasma etching removes at least 500 nm of material from the mechanically processed diamond surface.

15. A method according to claim 1, wherein the plasma etching removes at least 1000 nm of material from the mechanically processed diamond surface.

16. A method according to claim 1, wherein the roughness $R_q$ of the plasma etched surface is less than 0.5 nm.

17. A method according to claim 1, wherein the roughness $R_q$ of the plasma etched surface is less than 0.3 nm.

18. A method according to claim 1, wherein the roughness $R_q$ of the plasma etched surface is less than 0.2 nm.

19. A method according to claim 1, wherein the roughness $R_q$ of the plasma etched surface is less than 0.1 nm.

* * * * *

UNITED STATES PATENT AND TRADEMARK OFFICE
CERTIFICATE OF CORRECTION

PATENT NO. : 9,034,200 B2
APPLICATION NO. : 12/523956
DATED : May 19, 2015
INVENTOR(S) : Chee-Leong Lee et al.

Page 1 of 1

It is certified that error appears in the above-identified patent and that said Letters Patent is hereby corrected as shown below:

On the Title Page:

Item (73) "Element Six Limited Technologies Limited" should be corrected to read -- Element Six Technologies Limited --

Signed and Sealed this
Thirty-first Day of May, 2016

Michelle K. Lee
*Director of the United States Patent and Trademark Office*